(12) United States Patent
Nanba et al.

(10) Patent No.: US 8,437,841 B2
(45) Date of Patent: May 7, 2013

(54) LIVING BODY INSPECTION APPARATUS, AND RELEVANT METHOD AND PROGRAM PRODUCT

(75) Inventors: Shinji Nanba, Kariya (JP); Kazuhiro Sakai, Toyoake (JP); Katsuyoshi Nishii, Okazaki (JP); Toshiaki Shiomi, Nagoya (JP)

(73) Assignees: DENSO CORPORATION, Kariya (JP); Toshiaki Shiomi, Nagoya (JP)

( * ) Notice: Subject to any disclaimer, the term of this patent is extended or adjusted under 35 U.S.C. 154(b) by 449 days.

(21) Appl. No.: 12/717,574

(22) Filed: Mar. 4, 2010

(65) Prior Publication Data

US 2010/0228139 A1   Sep. 9, 2010

(30) Foreign Application Priority Data

Mar. 9, 2009   (JP) .................................. 2009-55447

(51) Int. Cl.
*A61B 5/0452* (2006.01)
*A61B 5/04* (2006.01)

(52) U.S. Cl.
USPC .......................................... 600/516; 600/508

(58) Field of Classification Search .................. 600/508, 600/509, 516
See application file for complete search history.

(56) References Cited

U.S. PATENT DOCUMENTS

| 7,734,334 | B2 * | 6/2010 | Mietus et al. ................. 600/513 |
| 2005/0076908 | A1 * | 4/2005 | Lee et al. ................. 128/204.23 |
| 2007/0032733 | A1 | 2/2007 | Burton | |

* cited by examiner

*Primary Examiner* — Allen Porter, Jr.
(74) *Attorney, Agent, or Firm* — Posz Law Group, PLC

(57) ABSTRACT

In a living body inspection apparatus to inspect RLS (Restless Legs Syndrome), a pulse interval is obtained from a pulse wave signal, thereby performing a frequency analysis of the obtained pulse interval using CDM. From a result of the frequency analysis, the low frequency components ranging from 0.04 to 0.15 Hz and the high frequency components ranging from 0.15 to 0.4 Hz are extracted. A value of low frequency components (LF)/high frequency components (HF) is obtained as an index to which an amendment based on age is applied. It is then determined whether LF/HF is equal to or greater than a predetermined determination value indicating RLS. For example, it is determined whether LF/HF is equal to or greater than 0.65, which suspects RLS. It is determined whether a signal is accurately calculated which indicates an activity of autonomic nerve. A state of RLS is determined using LF/HF.

10 Claims, 12 Drawing Sheets

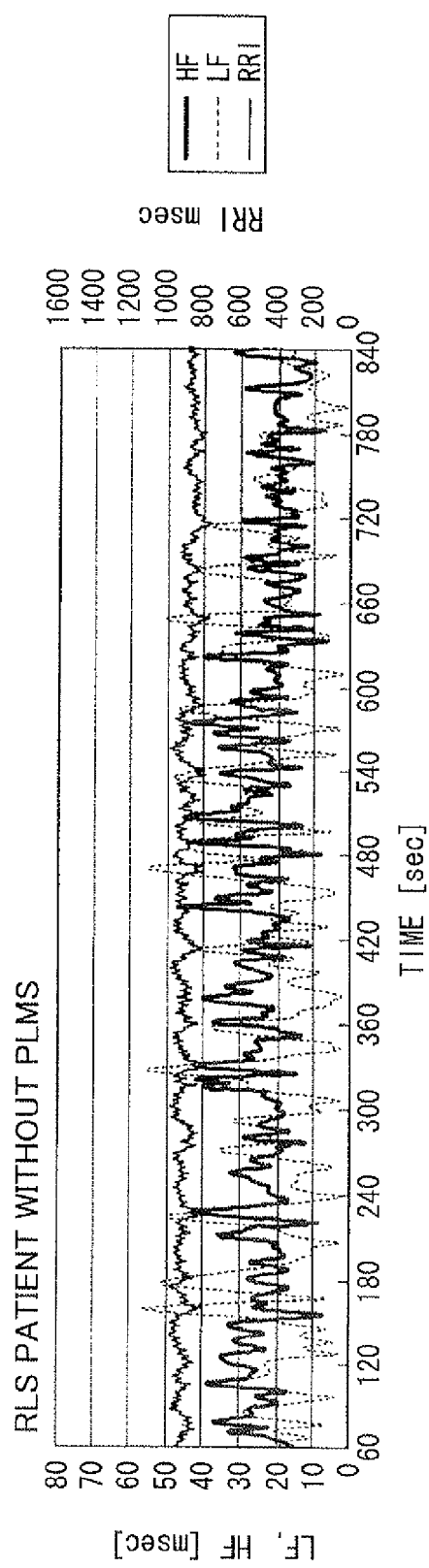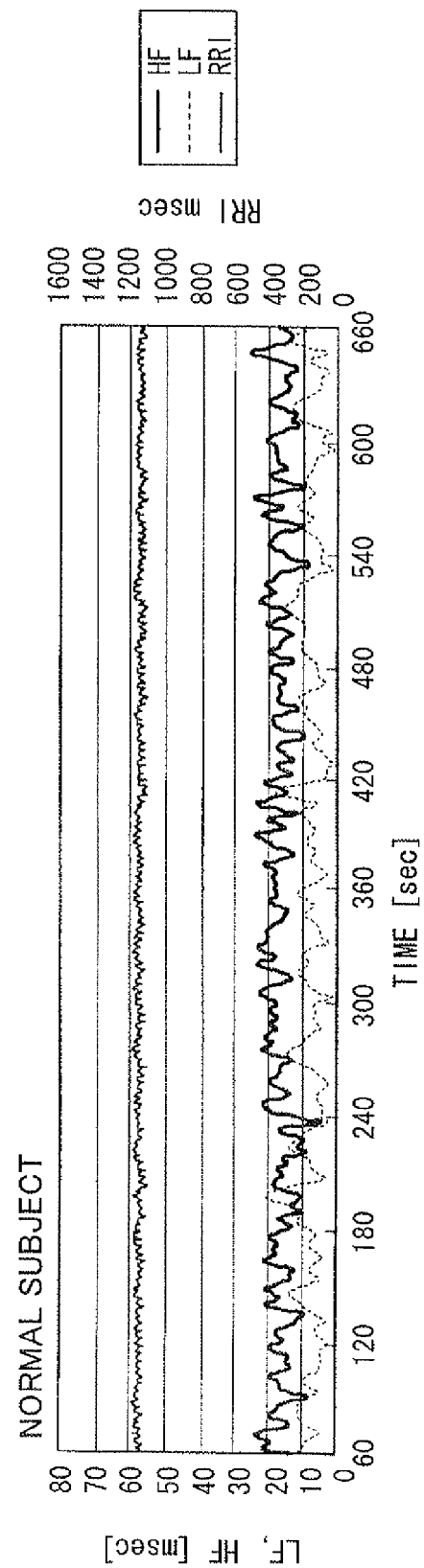

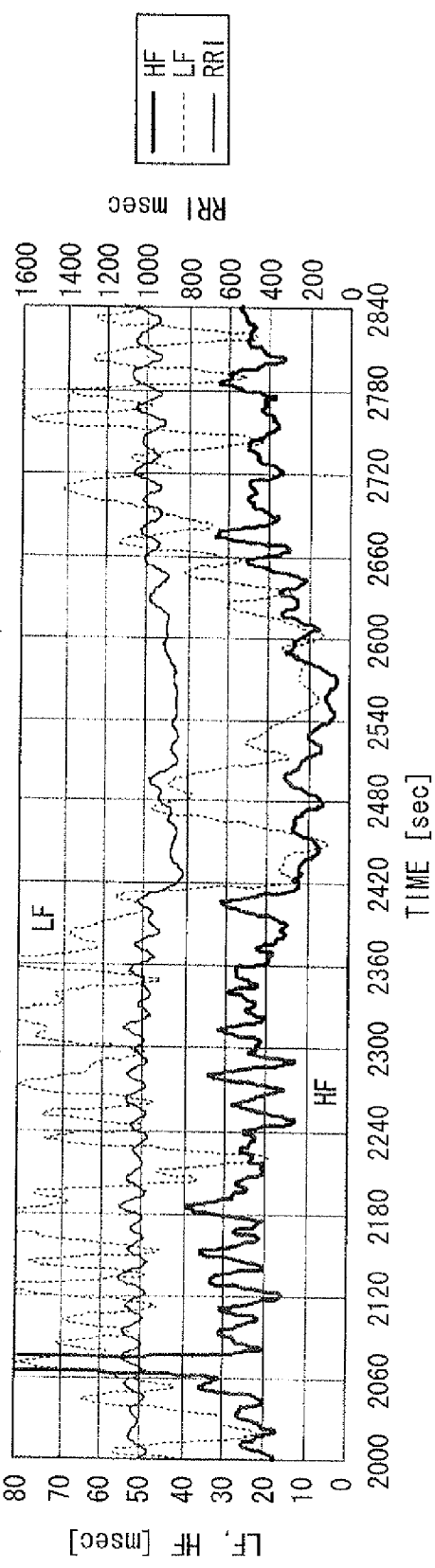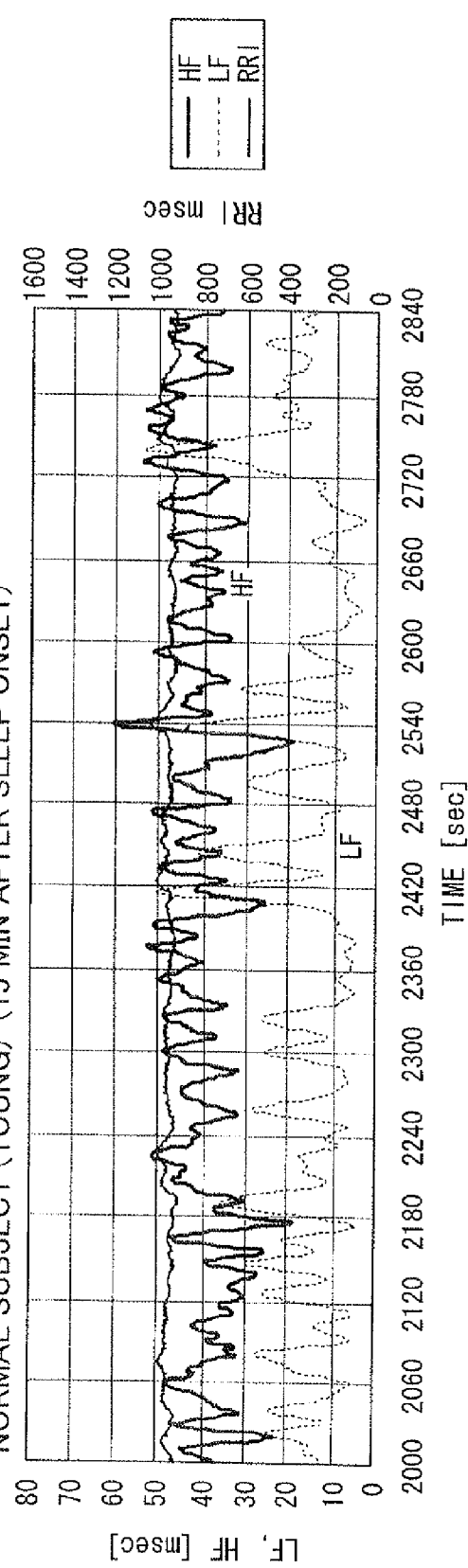

LIVING BODY INSPECTION APPARATUS, AND RELEVANT METHOD AND PROGRAM PRODUCT

CROSS REFERENCE TO RELATED APPLICATION

The present application is based on and incorporates herein by reference Japanese Patent Application No. 2009-55447 filed on Mar. 9, 2009.

FIELD OF THE INVENTION

The present invention relates to a living body inspection apparatus to inspect a restless legs syndrome (RLS) objectively, and a relevant method and program product.

BACKGROUND OF THE INVENTION

[Patent document 1] JP-2007-517553 T (US20070032733 A1)

The term restless legs syndrome (referred to as RLS) was created by neurologist Ekbom of Sweden in 1945. RLS is a neurological disease classified into a dyskinesia and has been an issue as a modern disease at home and abroad since the 21st century.

In Japan, RLS is called "muzu-muzu (signifying creepy) legs syndrome." RLS provides an unpleasant feeling centering on a leg, which is accompanied by an unpleasant and intolerable dysesthesia/paresthesia (crawly/creepy/aching) in a leg. The impulse (i.e., desire) of wanting to move a leg becomes strong at night, thereby causing insomnia. RLS is thus classified into a somnipathy or sleep disorder.

The unpleasant feeling of the leg can be relieved by moving or massaging the leg. In contrast, if being left still as it is, the unpleasant feeling worsens as the night progresses. The RLS patients in Japan are inferred to be about 4,700,000 people, which is 2 to 5% of the population. The prevalence rate of RLS rises with aging, thus exhibiting the peak at 60 to 70 years old. The male-female ratio is 1:1.5. The prevalence rate of RLS is inferred to increase in the near future as society ages.

Further, 80% of RLS patients are accompanied by periodic limb movements during sleep (referred to as PLMS or PLM during sleep), whereas 20% are not accompanied by PLMS. Therefore, the RLS diagnosis at the present time is largely dependent on the complaint centering on the sense of discomfort. For example, there is a technology (refer to Patent document 1) which detects a breathing disorder during sleep. In contrast, there is no objective and quantitative diagnostic method of RLS presently.

As explained above, PLM during sleep at night is observed in about 80% of RLS.

The all-night sleep polygraph inspection (polysomnography: PSG) is thus considered to be indispensable for diagnosis of RLS. The PSG inspection detects periodic stress (i.e., periodic limb movements: PLM) of muscles which appears in an electromyograph attached to a leg, thereby detecting RLS.

However, RLS is a condition mainly produced during sleep. Until the condition of a disease advances to some extent to thereby reach a level where the restless sense is recognized, any petition (complaint) is not obtained from a person himself/herself. In addition, when there are no self-defined symptoms, no one notices that RLS causes a sleep disorder (sleepiness). Therefore, a motivation to undergo the PSG inspection is not produced. Thus, early diagnosis is not easily achieved.

Furthermore, the PSG inspection requires a surveillance monitoring requiring one night of admission to a hospital, and obtains no diagnosis with respect to the RLS patient having no PLMS, thus possibly resulting in useless inspection.

That is, about 20% of RLS patients do not exhibit PLMS. Even if having the restless sense in the legs, the legs of those people do not actually move periodically. Thus, even if those people undergo the PSG inspection, RLS of those people cannot be detected. Therefore, under the present circumstances, the confirmation of the effect of medical treatment such as using medicine depends on the subjectivity of the person himself/herself.

In addition, the prevalence rate of RLS is 2 to 5% of a population, which is considered to be significantly great, thereby making it very difficult to execute the PSG inspection for all the diseased people. Such a circumstance requires a development of new techniques such as an inspection apparatus to detect dysesthesia/paresthesia of the leg in determination items other than PLMS while allowing medical practitioners to objectively evaluate curative effects, and a new home simple monitor to use PLMS for screening.

SUMMARY OF THE INVENTION

The present invention is made so as to address the above issue. It is an object of the present invention to provide a living body inspection apparatus to inspect RLS using a simple technique, and related method and program product.

It is noted that RLS is related to an activity amount of an autonomic nerve (sympathetic nerve) in respect of whether to be present or absence, or the degree of the presence. The present inventors obtain a study result that investigating of a variation component of heart rate (heart rate variability: HRV, or heartbeat fluctuation or variation) correlated with an autonomic nerve activity enables the detection as to whether RLS is present or absent or as to the degree of RLS. Such knowledge allowed achievement of the present invention.

To achieve the above object, according to an example of the present invention, a living body inspection apparatus is provided as follows. An interval calculation section is configured to obtain a heartbeat interval from a signal which indicates a heartbeat variation. A variation state calculation section is configured to calculate an index which indicates a variation state of the heartbeat interval calculated by the interval calculation section. A comparison section is configured to compare the index, which indicates the variation state of the heartbeat interval calculated by the variation state calculation section, with a predetermined reference value. A determination section is configured to determine a state of a restless legs syndrome, which is represented by RLS, based on a result of comparing by the comparison section.

The present inventors' research has determined that with respect to RLS, the presence or absence or the degree of disease (i.e., symptom) (severe, middle, or mild) has a significant correlation with a heart rate variability or heartbeat variation. Thus, the presence or absence, or disease degree of RLS are detectable easily and sufficiently accurately by comparing an index indicating a heart rate variability or heartbeat variation (i.e., an index of which the value changes depending on the heart rate variability) with the reference value (for example, reference value acquired by the data from the healthy person, research, etc.), even in cases that the PSG inspection is not conducted, or furthermore, even with respect to test subjects exhibiting no PLMS (periodic limb movements during sleep).

It is noted that a signal for indicating a heartbeat variation includes a signal which changes according to the heartbeat variation such as a signal of electrocardiography, a signal of pulse wave, a signal of blood pressure. Therefore, the sensor which detects a signal for indicating the heartbeat variation includes a pulse wave sensor (plethysmograph), an electrocardiography sensor (electrocardiograph), a heart rate meter, a pulsometer, a blood flow meter, and a continuous sphygmomanometer.

According to another example of the present invention, a method is provided for determining a state of a restless legs syndrome, which is represented by RLS, using a living body inspection apparatus. The method comprises: obtaining a heartbeat interval from a signal which indicates a heartbeat variation; calculating an index which indicates a variation state of the calculated heartbeat interval; comparing the index, which indicates the variation state of the calculated heartbeat interval, with a predetermined reference value; and determining a state of RSL based on a result of the comparing the index with the predetermined reference value.

Relating to this example, as yet another example of the present invention, a program product stored in a computer readable medium comprising instructions being executed by a computer is provided, wherein the instructions include the above mentioned method for determining the state of the restless legs syndrome, i.e., RLS, and the method is computer-implemented.

Such a program product can be stored in a computer-readable storage medium such as a flexible disk, a magnetic disk, magneto-optical disc, a CD-ROM, a hard disk, and memory card; the program product stored in the storage medium can be read out and loaded in a computer system and activated as needed.

In addition, the program product can be stored in a computer-readable storage medium such as a ROM, a backup RAM, which is built-in a computer system.

BRIEF DESCRIPTION OF THE DRAWINGS

The above and other objects, features, and advantages of the present invention will become more apparent from the following detailed description made with reference to the accompanying drawings. In the drawings:

FIG. 4A is a graph illustrating signals of an RLS patient without PLMS;

FIG. 4B is a graph illustrating signals of a normal subject;

FIG. 6A is a graph illustrating signals of an RLS patient with PLMS;

FIG. 6B is a graph illustrating signals of a normal subject;

DETAILED DESCRIPTION OF THE PREFERRED EMBODIMENTS

The following explains a living body inspection apparatus, and related program and storage medium according to examples of an embodiment of the present invention with reference to drawings.

Figure 1:
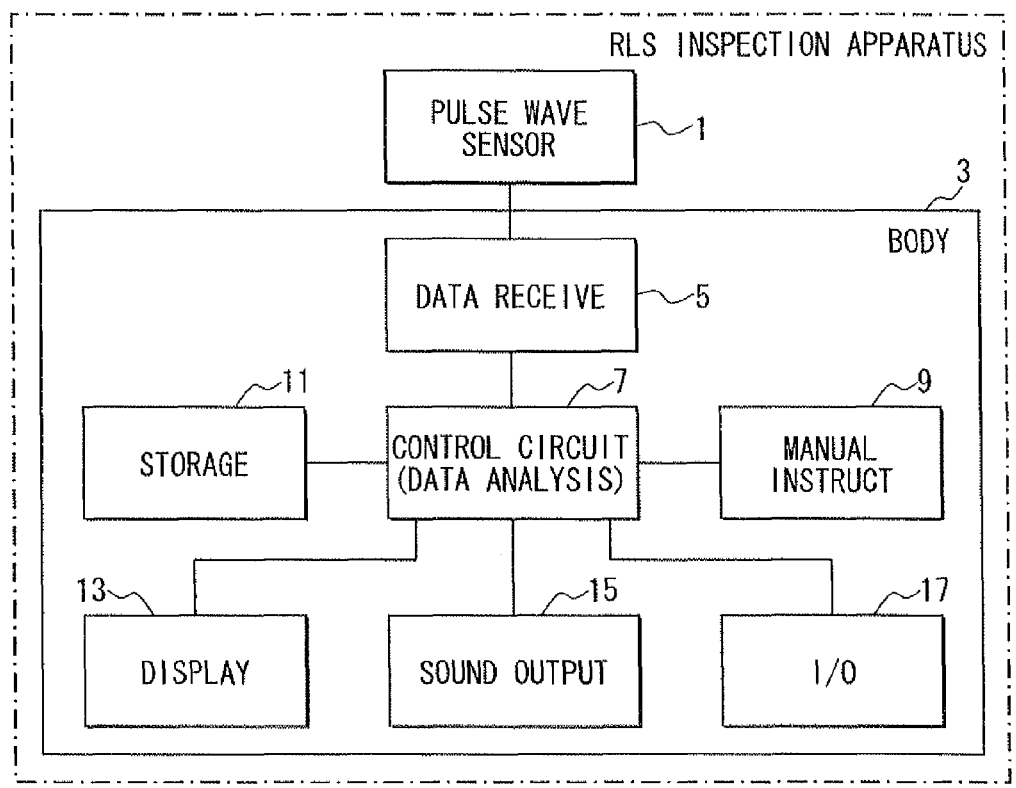
FIG. 1 is a block diagram illustrating a main configuration of an RLS inspection apparatus according to a first example of an embodiment of the present invention.
Figure 2:
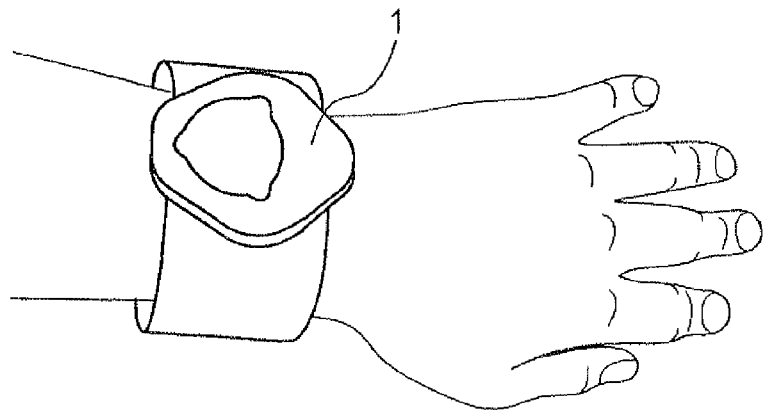
FIG. 2 is a diagram for explaining an attachment state of a pulse wave sensor.

First Example a) The following explains a basic configuration of a living body inspection apparatus (referred to as an RLS inspection apparatus hereafter) which detects RLS (Restless Legs Syndrome) or its symptom according to a first example of the present embodiment with reference to FIG. 1 and FIG. 2. As illustrated in FIG. 1, the RLS inspection apparatus includes the following: a pulse wave sensor 1 (refer to FIG. 2) which is attached to a human body for detecting a pulse wave; and a main body portion 3 which executes various kinds of computations based on measurement data of the pulse wave sensor 1. Furthermore, the configuration or function of the main body portion 3 may be incorporated into the pulse wave sensor 1.

It is noted that the pulse wave sensor 1 is a known optical reflection type sensor which has a light emitting element (for example, a light emitting diode: LED) and a light receiving element (photo diode: PD) for detecting a variation of blood flow amount as a variation of a pulse wave.

The pulse wave sensor 1 emits light toward a human body from the light emitting element, receives (an amount of) the reflection light, which changes according to the light absorbed by the hemoglobin in the human body, using the photo receiving element, and generates a pulse wave signal (e.g., voltage signal) from the variation of the received amount of the reflection light.

Furthermore, the pulse wave sensor 1 is used for outputting a pulse wave signal corresponding to a heart rate. Without need to be limited thereto, as long as detecting a heart rate variability, or obtaining a signal corresponding to a heart rate, any sensor may be used. For instance, an electrocardiography sensor to detect a heart rate, or a blood pressure sensor to detect a blood pressure may be used.

In contrast, the main body portion 3 includes the following: a data receiving device 5 which receives data indicating a pulse wave signal transmitted from the pulse wave sensor 1 (using wireless or wired communications link); a control circuit 7 mainly including a microcomputer and functioning as a data analysis device 7 to analyze the data received in the data receiving device 5; a manual instruction device 9 which receives various kinds of manual instructions or operations; a storage device 11 to store a variety of data; a display device 13 to display an analysis result etc. which is analyzed in the data analysis device 7; a sound output device 15 such as a speaker 15 to output sounds or vocal sounds; and an input/output (I/O) device 17 to output and input data with an external device.

Figure 3:
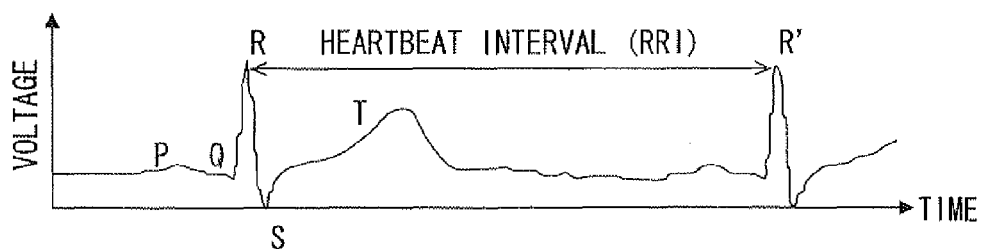
FIG. 3 is a graph that illustrates an example of an electrocardiogram.

In the present example, a pulse interval corresponding to a heart rate variability or heartbeat fluctuation or variation (in detail, the heartbeat interval RRI (R wave-R wave Interval)

illustrated in FIG. 3) is obtained from the pulse wave signal, an index for detecting RLS is obtained based on the variation in the pulse interval, and RLS is detected based on the index.

Furthermore, the data of the pulse wave signal can be transmitted to the main body portion 3 from the pulse wave sensor 1. In contrast, the pulse wave sensor 1 may contain a built-in microcomputer to execute a part of the process of the data analysis device 7. For example, the pulse wave sensor 1 may obtain the data of the pulse interval from the pulse wave signal, and transmit the obtained data to the main body portion 3 for subsequent RLS detection.

In addition, the data communications link from the pulse wave sensor 1 to the main body portion 3 may be achieved by a wired tangible communications link or a wireless communications link. Furthermore, the data of the pulse wave sensor 1 may be once stored in a memory device such as a USB memory or a memory card, and such a memory device may be attached or inserted into the main body portion 3.

b) The following explains a principle of the RLS detection in the present example. The developmental mechanism of RLS is not understood well. It is thought that it results from an anomaly in an autonomic nervous system. The present inventors have determined that there is a high correlation between (i) RLS and (ii) an index indicating an autonomic nerve activity. Therefore, in the present example, the presence or absence, or the degree of RLS is detected by using the index which indicates the autonomic nerve activity.

FIGS. 4A, 4B are graphs illustrating, with respect to each of (i) an RLS patient and (ii) a normal subject of the similar age (around 60 years old), an investigation result of low frequency components (LF: an integral value of the power of 0.04 to 0.15 Hz) obtained by conducting a frequency analysis of the heartbeat interval (RRI) with CDM (Complex DeModulation), and high frequency components (HF: an integral value of a power of 0.15 to 0.4 Hz). It is noted that the boundary value such as 0.15 Hz between LF and HF is treated as belonging to the high frequency components.

The graphs illustrate that the data of the RLS patient exhibits greater variations in the heartbeat interval, low frequency components, and high frequency components, than the data of the normal subject. In particular, the variation in the low frequency components can be found to be great. Therefore, the state of RLS can be detected based on the states of the variations, in particular, based on the variation of the low frequency components. The following explains more specifically.

Figure 5:
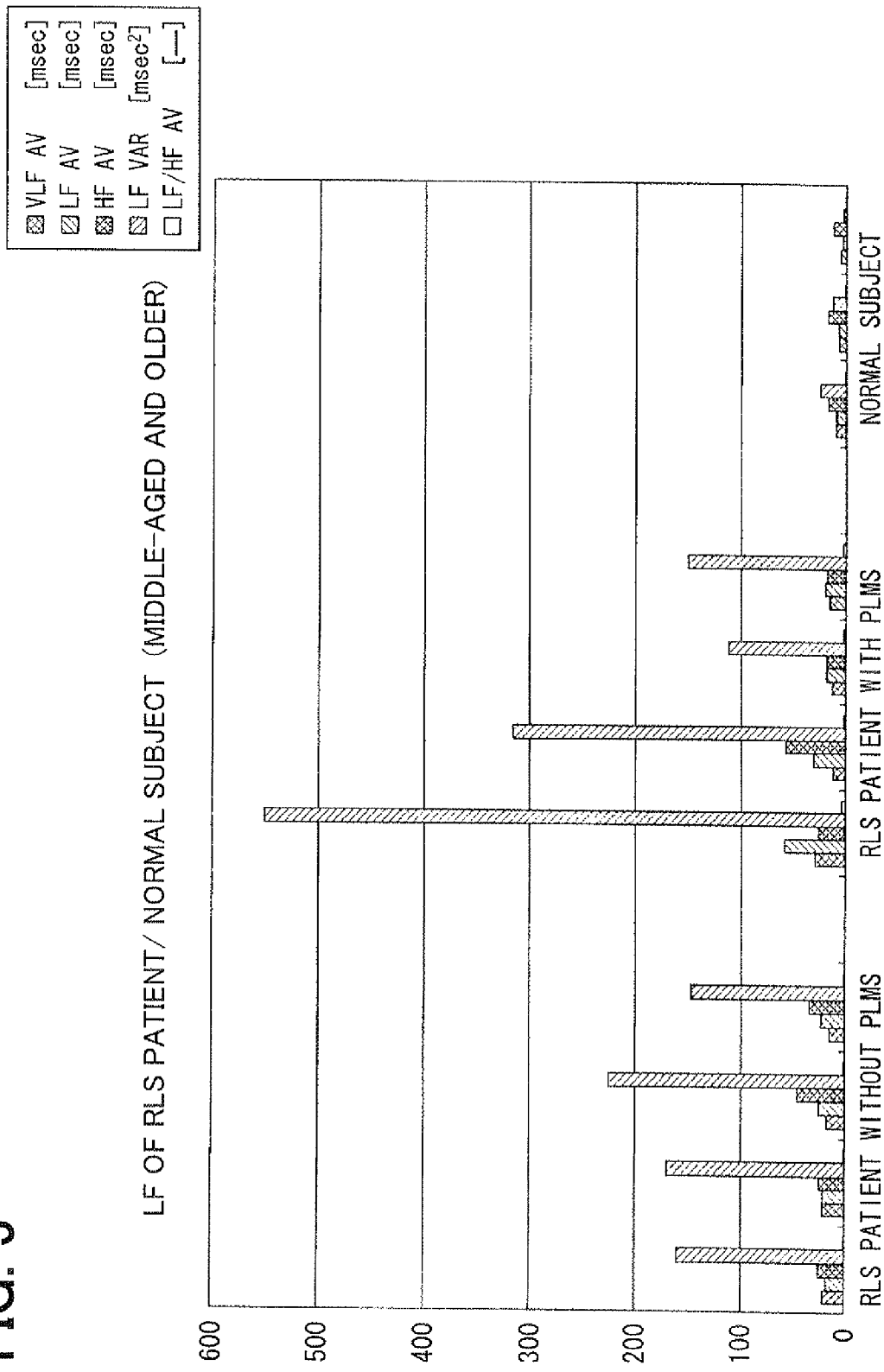
FIG. 5 is a graph which illustrates comparison of an RLS patient and a normal subject in respect of LF components.

FIG. 5 illustrates an investigated result including a variety of data in comparison with respect to eleven test subjects of persons in middle or advanced ages (44 to 67 years old) of the same generation. In detail, the target test subjects are (1) patients each having RLS complain (without PLMS) (also referred to as an RLS patient without PLMS), (2) patients each having RLS complain (with PLMS) (also referred to as an RLS patient with PLMS), and (3) normal subjects or healthy people. The indices, which are investigated, are (i) VLF average (average of very low frequency components of 0.003 to 0.04 Hz), (ii) LF average (average of low frequency components of 0.04 to 0.15 Hz), (iii) HF average (average of high frequency components of 0.15 to 0.4 Hz), (iv) LF variance (variance of low frequency components LF), and (v) LF/HF average (average of the ratio of low frequency components to the high frequency components). The average signifies an average of individual frequency components for a ten-minutes period.

The result indicates the difference in each index (for example, LF) among (1) the patients having RLS complain (without PLMS), (2) the patients having RLS complaint (with PLMS), and (3) the normal subjects (control or reference). Therefore, the determination as to RLS can be executed based on the respective indices.

That is, the frequency analysis of the heartbeat interval (RRI) is conducted, for example, using the well-known CDM (Complex DeModulation). The obtained low frequency components differ greatly between the RLS patients and the normal subjects who are not an RLS patient. Therefore, RLS is detectable using the low frequency components (or index based on the low frequency components).

In this regard, however, each index mentioned above such as LF, changes depending on an age. The following explains an amendment based on ages. FIGS. 6A, 6B are graphs illustrating an actually investigated result of normal subjects or healthy persons of a young generation (i.e., the age group of those in their twenties) and RLS patients of a middle-aged and elderly generation (i.e., the age group of those in their fifties) in respect of the heartbeat interval, low frequency components, and high frequency components.

The graphs indicate that the great variations of the low frequency components and the high frequency components are demonstrated even in the young generation having no RLS. Therefore, the accurate determination may not be able to be performed only by investigating the low frequency components etc., without taking ages or generations into consideration. That is, in order to detect RLS with sufficient accuracy, it turns out that it is necessary to add an age-based amendment (for example, distinction of persons of middle-aged and elderly generation or young generation).

Figure 7:
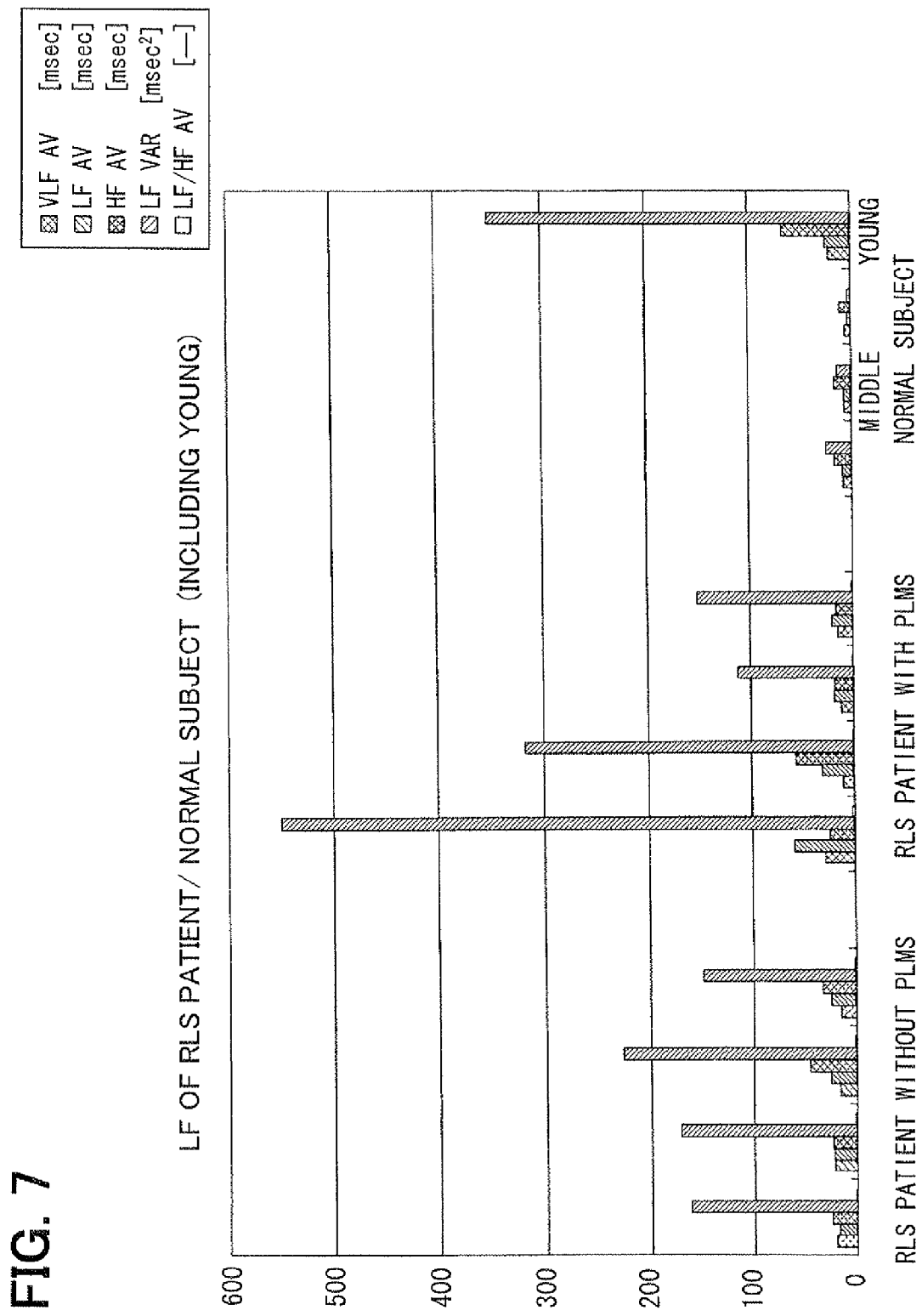
FIG. 7 is a graph which illustrates comparison of an RLS patient and a normal subject in respect of LF components.

FIG. 7 illustrates an investigated result including a variety of data in comparison with respect to eleven test subjects of persons in a middle-aged and elderly generation (44 to 67 years old) and in a young generation (twenties). In detail, the target test subjects are (1) patients each having RLS complain (without PLMS) (also referred to as an RLS patient without PLMS), (2) patients each having RLS complain (with PLMS) (also referred to as an RLS patient with PLMS), and (3) normal subjects or healthy persons. The investigated indices are the VLF average, LF average, HF average, LF variance, and LF/HF average.

As a result, the LF of (1) the RLS patient (without PLMS) and the LF of (2) the RLS patient (with PLMS) are higher than the LF of (3) the normal subjects in the middle-aged and elderly generation, thus exhibiting a significant difference in LF between the RLS patients and the normal subjects in the middle-aged and elderly generation. However, the LF of the healthy young generation is high like that of the RLS patients. Thus, there is a possibility to reduce the accuracy of detection of RLS if only the LF is used.

Figure 8:
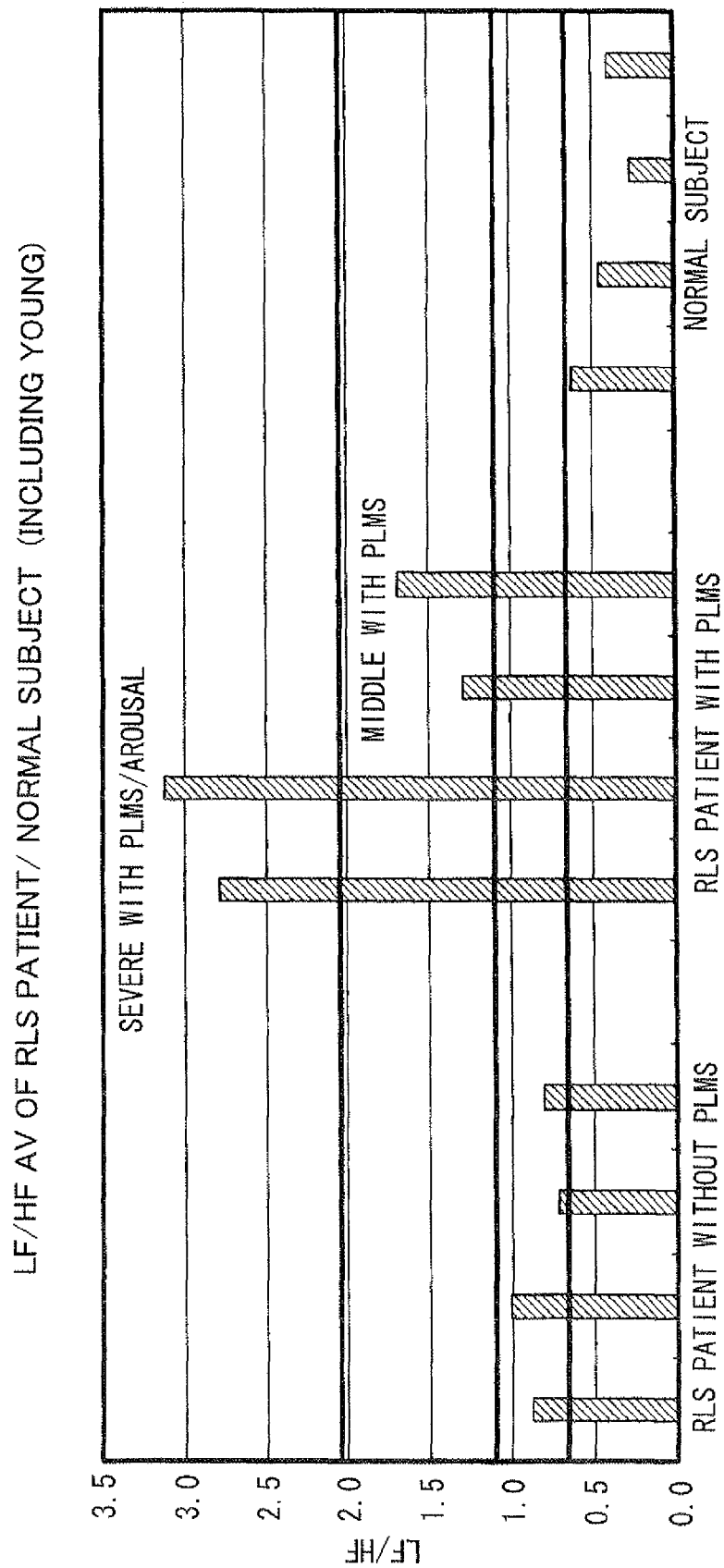
FIG. 8 is a graph which illustrates comparison of a RLS patient and a healthy person in respect of LF/HF.

Therefore, in order to eliminate the influence due to the difference in the age, LF/HF may be used as an index for the RLS detection, as illustrated in FIG. 8. Furthermore, FIG. 8 enlarges the portions corresponding to the LF/HF average among the data in FIG. 7.

As clearly understood from FIG. 8, the use of the LF/HF average can distinguish the RLS patients from the normal subjects belonging to either the middle-aged and elderly generation or the above mentioned young generation, thereby providing a highly accurate RLS detection.

That is, the use of the LF/HF average can clearly distinguish (1) patients each having RLS complain (without PLMS) (also referred to as an RLS patient without PLMS), (2) patients each having RLS complain (with PLMS) (also referred to as an RLS patient with PLMS), and (3) normal subjects or healthy people. Further, with respect to (2) patients having RLS complain (with PLMS), the severely diseased person accompanied by arousal and the middle diseased person accompanied by no arousal are distinguishable or determined by the use of LF/HF ratio. Such determination is made as follows: the LF/HF equal to or less than 0.65 corresponding to (3) normal subjects or healthy persons; the LF/HF ranging between 0.65 and 1.1 corresponding to (1) patients having RLS complain (without PLMS); the LF/HF ranging between 1.1 to 2.0 corresponding to (2) the middle-diseased patients with PLMS; and the LF/HF equal to or greater than 2.0 corresponding to the severe patients with PLMS.

Furthermore, in the above, the presence or absence of awakening is investigated by monitoring an electroencephalogram, while the presence or absence of PLM is investigated by an electromyograph attached to a leg.

c) The following explains an RLS detection process executed by the control circuit 7 functioning as the data analysis device based on a principle of the above mentioned RLS detection. It is further noted that a flowchart or the processing of the flowchart in the present application includes sections (also referred to as steps), which are represented, for instance, as S100. Further, each section can be divided into several sub-sections while several sections can be combined into a single section. Furthermore, each of thus configured sections can be referred to as a means or unit and achieved not only as a software device but also as a hardware device.

The present process is executed to detect RLS from the variation state of the pulse interval corresponding to the heartbeat interval using the pulse wave sensor 1.

(1) An initial process is explained below.

The present process is executed to precede the actual inspection of RLS.

Figure 9:
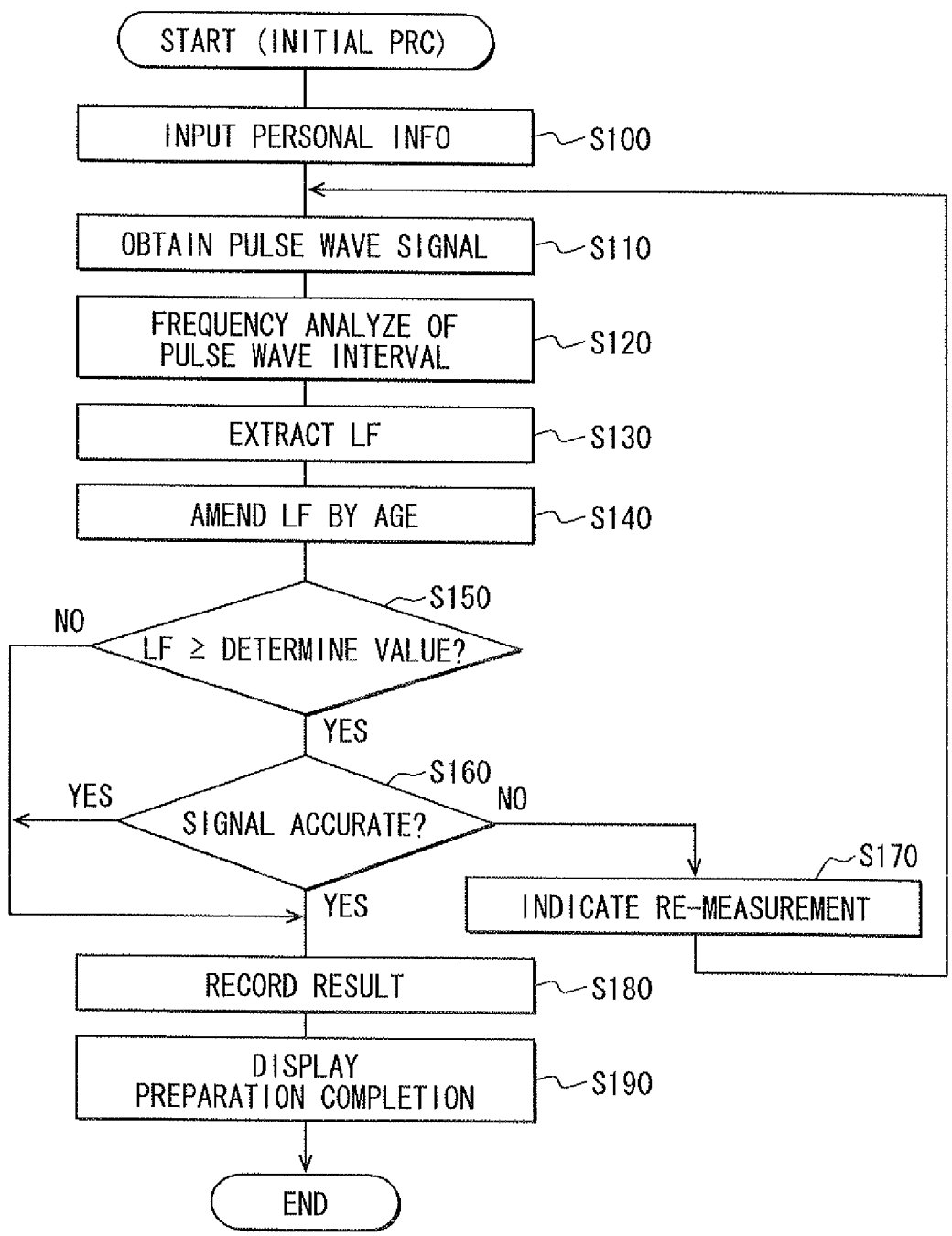
FIG. 9 is a flowchart illustrating an initial process, which precedes an actual inspection of RLS.

As illustrated in the flowchart of FIG. 9, at S100, personal information such as an age, sex, and weight is inputted.

At S110, a pulse wave signal measured in a resting state (lasting at least three minutes) is obtained by the pulse wave sensor 1. At S120, pulse intervals (corresponding to the heartbeat intervals) are obtained from the pulse wave signals and the obtained pulse intervals are subjected to the frequency analysis using CDM (Complex DeModulation).

At S130, the low frequency components of 0.04 to 0.15 Hz are extracted from the result of the frequency analysis, for example. That is, an integral value of the power of the frequency range is calculated. At S140, an age amendment is made for the low frequency components. For example, the index of the low frequency components/whole-frequency components (LF/ALL) or the index of the low frequency components/high frequency components (LF/HF) are is obtained. Further, the low frequency components of the test subject/the low frequency components of the normal subject of the age group or generation similar to that of the test subject (LF1/LF2) is calculated to thereby obtain an index to which an amendment based on age is applied. Hereinafter, this index may be referred to as an age-amended index.

At S150, it is determined whether the age-amended index is equal to or greater than a predetermined determination value indicating RLS. When the affirmative determination is made at S150, the processing proceeds to S160. In contrast, when the negative determination is made at S150, the processing proceeds to S180.

At S160, it is determined whether a signal is accurately calculated which indicates an activity of autonomic nerve (sympathetic nerve). That is, it is determined whether an unusual value appears, for example, under the influence of a mistake in the attachment or mounting of the pulse wave sensor 1. When the affirmative determination is made at S160, the processing proceeds to S180. In contrast, when the negative determination is made at S160, the processing proceeds to S170.

At S170, since the acquired signal is determined to be abnormal, instructions are issued to require a repeated attachment of the pulse wave sensor 1 and a re-measurement at the resting state, thereby returning the processing to S110. At S180, since it is determined that there is no mistake in the measurement, the personal information, the measurement signal, and the analysis result are stored in the storage device 11.

At S190, the display device 13 is caused to display a message "preparation for inspection is completed," then once ending the present process.

(2) The following explains a measurement process for an actual RLS detection.

Figure 10:
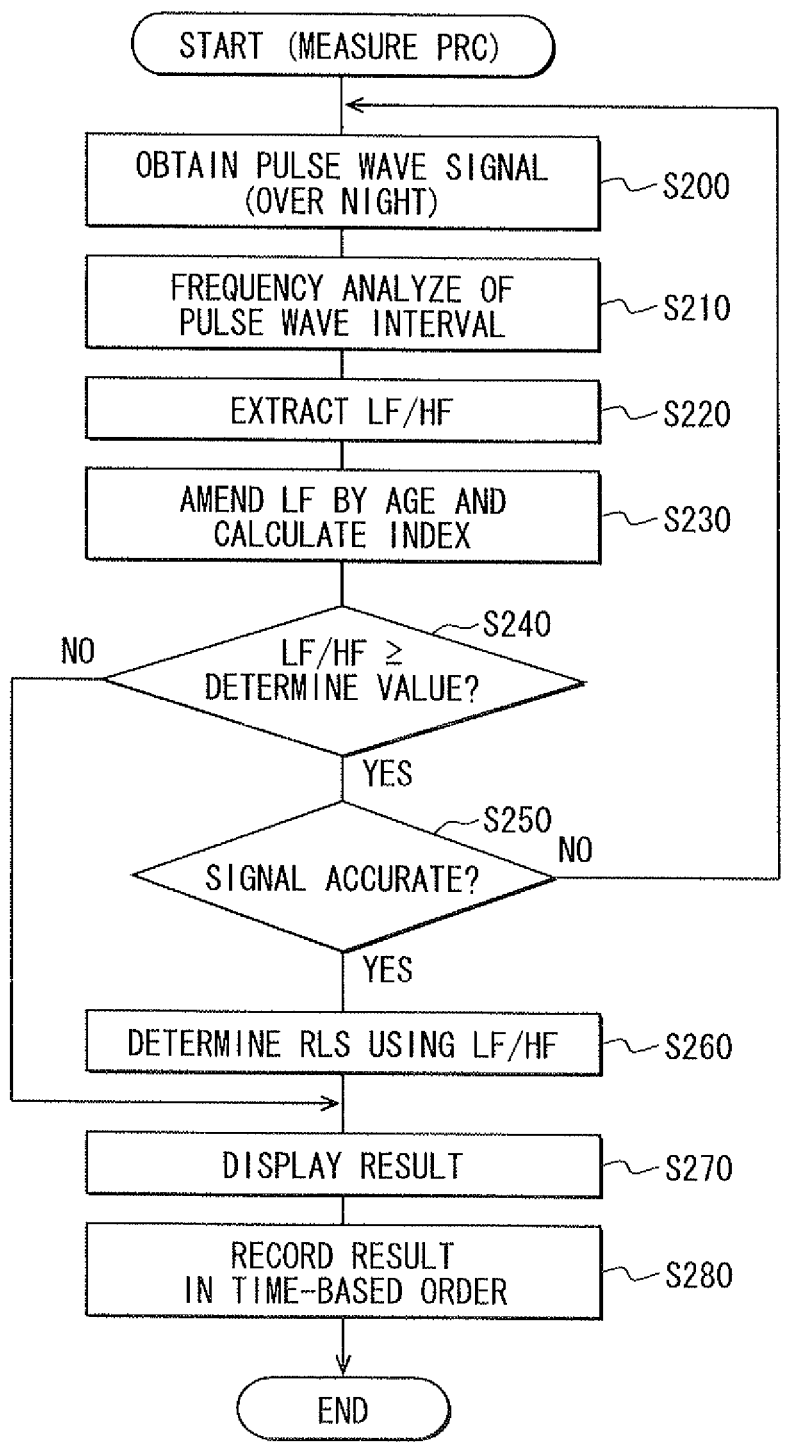
FIG. 10 is a flowchart illustrating a measurement process for an actual detection of RLS.

As illustrated in the flowchart of FIG. 10, at S200, pulse wave signals measured by the pulse wave sensor 1 over a night or during 24 hours are obtained. At S210, pulse intervals are obtained from the pulse wave signals and the obtained pulse intervals are subjected to the frequency analysis using CDM (Complex DeModulation).

At S220, the low frequency components of 0.04 to 0.15 Hz, and the high frequency components of 0.15 to 0.4 Hz are extracted from the result of the frequency analysis. At S230, an age amendment is made. At this time, as an age-amended index, low frequency components/high frequency components (i.e., LF/HF) is obtained.

At S240, it is determined whether the age-amended index (LF/HF) is equal to or greater than a predetermined determination value indicating RLS. For example, it is determined whether LF/HF is equal to or greater than 0.65, which suspects RLS or the presence of RLS. When the affirmative determination is made at S240, the processing proceeds to S250. In contrast, when the negative determination is made at S240, the processing proceeds to S270.

At S250, it is determined whether a signal is accurately calculated which indicates an activity of autonomic nerve. When the affirmative determination is made at S250, the processing proceeds to S260. In contrast, when the negative determination is made at S250, the processing returns to S200.

At S260, the state of RLS is determined using LF/HF. For example, as illustrated in the FIG. 8, the state of RLS corresponds to LF/HF. Thus, the determination is made as follows: the LF/HF ranging between 0.65 and 1.1 corresponding to (1) patients having RLS complain (without PLMS) (also referred to as RLS patients without PLMS); the LF/HF ranging between 1.1 to 2.0 corresponding to (2) the RLS middle-diseased patients with PLMS (also referred to as RLS patients with PLMS); and the LF/HF equal to or greater than 2.0 corresponding to (2) the RLS severe patients with PLMS and arousal (also referred to as RLS patients with PLMS and arousal). It is noted that the numerical values of the above determination are based on only the measurement data under sound sleep. When the measurement data during all the night contain data under halfway awakening or temporary body movement, it is necessary to make the above determination using the values raised about 10 to 30%.

At S270, the determination result of RLS is displayed. At S280, the personal information, the measurement signals, the analysis result, etc. are recorded in a time-based order. The present process is once ended.

Furthermore, the above sections or steps of the present process may be amended. For instance, the determination as to the presence or absence of RLS at S240 and the classification or determination as to the degree of RLS at S260 may be made simultaneously. It may be then determined whether a signal is accurately calculated. When it is accurately calculated, the result of the determinations such as the RLS determination may be displayed.

d) The following explains advantages or effects of the present example. In the present example, the frequency analysis of the pulse wave interval obtained from the pulse wave sensor 1 is conducted; then, the determination as to the presence or absence and/or the degree of RLS is made using the index of LF/HF. Therefore, compared with a conventional one, the inspection of RLS can be easily made by the simple technique.

In addition, the present example can achieve, with an improved accuracy, the determination of RLS even in cases that the PSG inspection is not conducted or the test subject has no PLMS, thereby providing a prominent effect. Furthermore, for example, the present example adopts an index such as LF/HF to thereby eliminate the influence of the age, therefore providing the more accurate determination of RLS also from such an aspect.

Furthermore, to raise the accuracy of determination, it is desirable to adopt the following:

(1) When arrhythmia is identified, the corresponding portion is eliminated.

That is, when there is found arrhythmia, it is difficult to accurately determine the variation of the pulse interval resulting from RLS. The data within the duration in which the arrhythmic is present is not used for the frequency analysis etc.

(2) Some sort or another sometimes causes the pulse interval to exceed the reference value for a certain duration. When there is no data during the certain duration, the analysis cannot be made with sufficient accuracy. In such cases, for instance, data just before the certain duration may be interpolated into the certain duration missing the data.

(3) The pulse interval may exceed the reference value continuously. In such cases, the interpolation cannot be used; thus, all the data are not used for the analysis.

Second Example

The following explains a second example of the embodiment while omitting portions similar to those of the first example.

a) The present inventers' research has determined that, of the low frequency components, the low frequency components of 0.03 to 0.09 Hz (referred to as RLSF) has a significant association or correlation with RLS.

Figure 11:
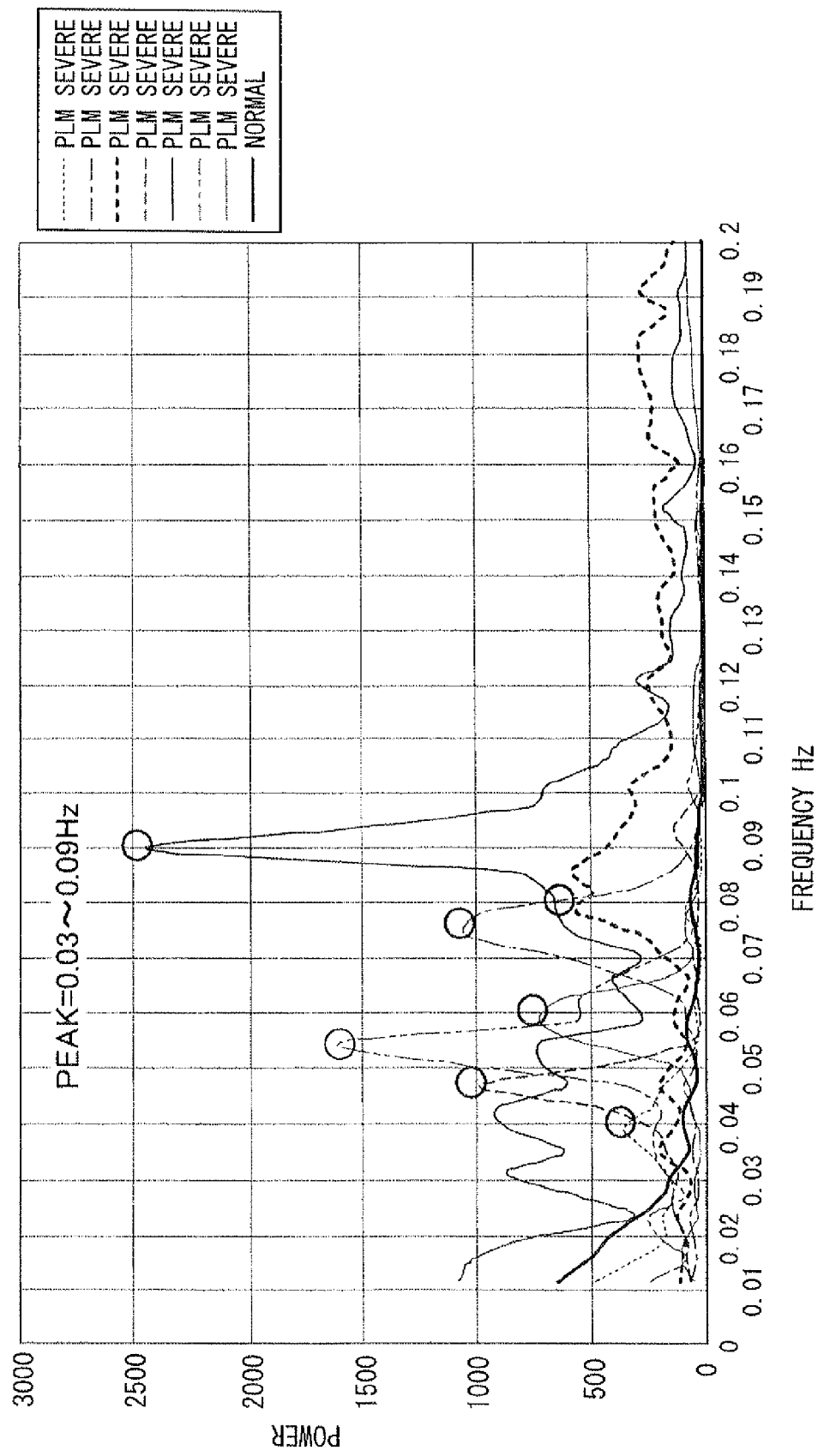
FIG. 11 is a graph illustrating a result of a frequency analysis of a heart rate variability of a PLM severe patient according to a second example of the embodiment.

FIG. 11 illustrates a result of a frequency analysis of heartbeat intervals relative to eight test subjects obtained from an electrocardiogram sensor. As clearly understood from FIG. 11, the severe diseased PLM patients (patient having PLM occurring frequently) have respective high peaks in the range of the specific low frequency components RLSF.

Figure 12:
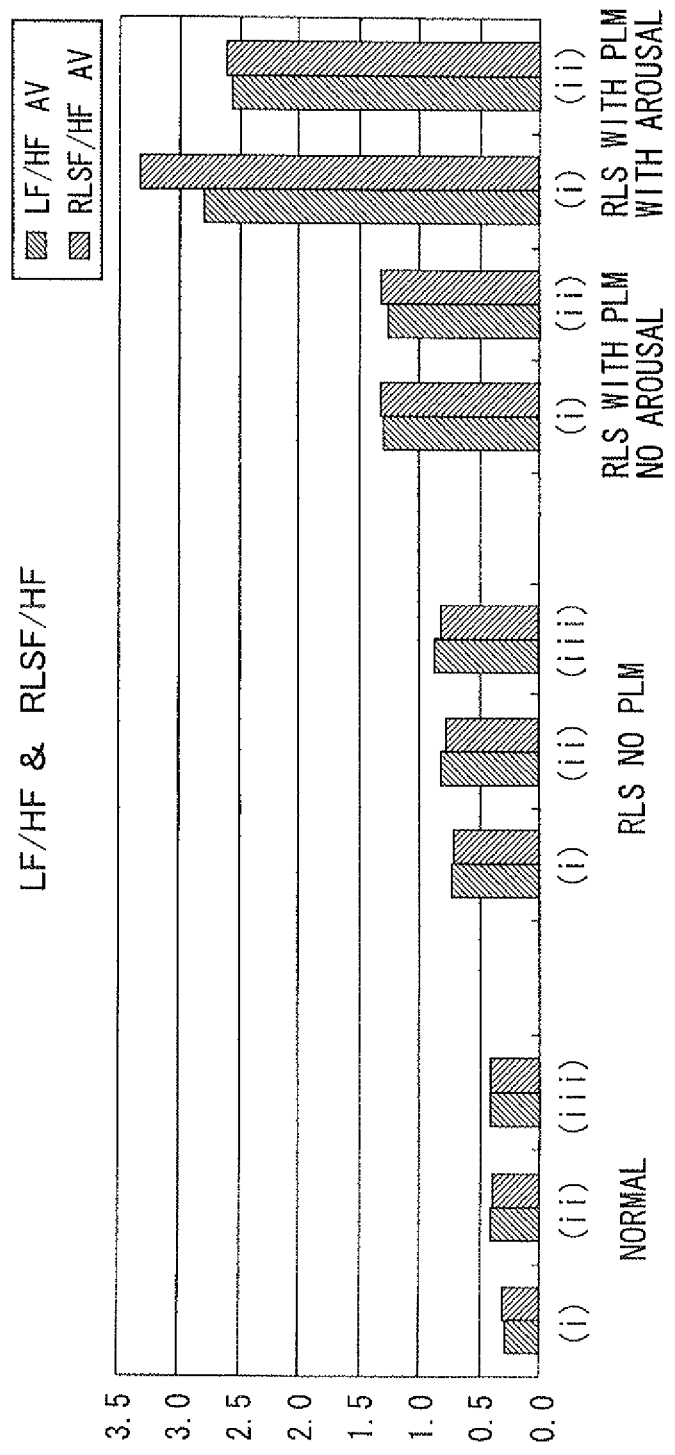
FIG. 12 is a graph illustrating a comparison result of LF/HF and RLSF/HF.

Therefore, using the specific low frequency components RLSF is effective for the determination of RLS. FIG. 12 compares the values of LF/HF and RLSF/HF with respect to eleven test subjects.

As clearly understood from FIG. 12, LF/HF and RLSF/HF are differentiated depending on the presence or absence, and/or the degree of RLS. That is, FIG. 12 indicates such relation or classification with respect to LF/HF and RLSF/HF, as follows:

Normal subject<0.5;
0.5<=RLS complaint alone (without PLM)<1.0;
1.0<=RLS with PLM (without arousal)<2.0;
2.0<=RLS with PLM (with arousal and sleep disorder).

Figure 13:
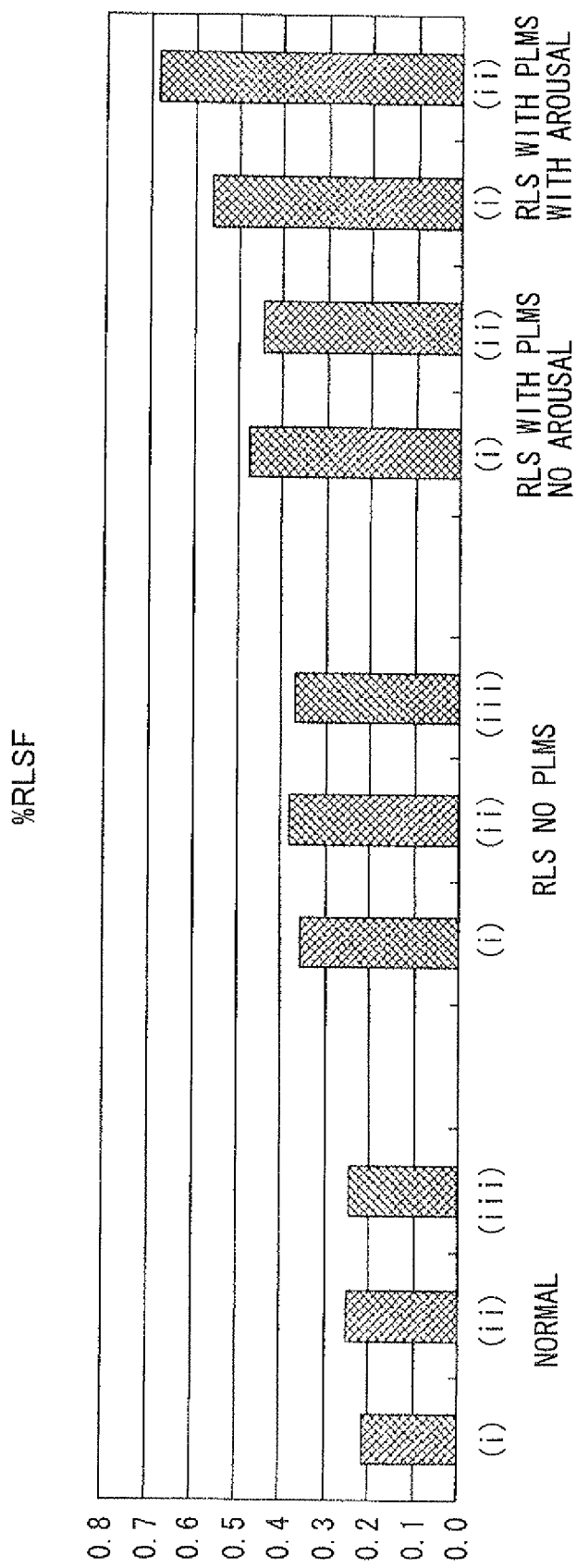
FIG. 13 is a graph illustrating a comparison result of % RLSF.

In particular, a value of RLSF/HF provides a difference slightly greater than LF/HF. RLSF/HF has an advantage to more easily separate patients with only RLS complaints from patients with PLM. FIG. 13 illustrates % RLSF (ratio of RLSF components=RLSF/(HLF+RLSF)). Furthermore, HLF corresponds to a range between 0.09 to 0.4 Hz.

FIG. 13 thus illustrates a relation or classification with respect to % RLSF as follows:

Normal subject<0.3;
0.3<=RLS complaint alone (without PLM)<0.4;
0.4<=RLS with PLM (without arousal)<0.5;
0.5<=RLS with PLM (with arousal).

b) Therefore, the following explains a process using RLSF. The present process is executed by the control circuit 7 functioning as the data analysis device. The following uses a pulse wave sensor by replacing the electrocardiography sensor. Without need to be limited thereto, the electrocardiography sensor can also be used also so as to directly acquire heartbeat intervals.

Figure 14:
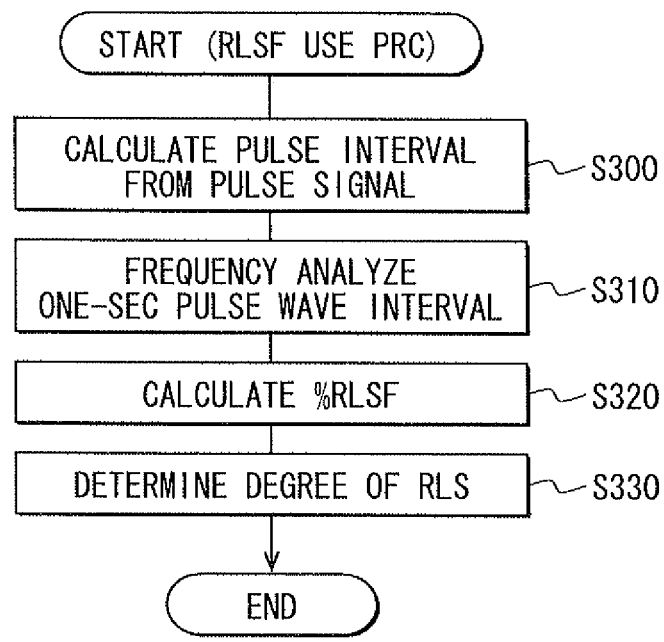
FIG. 14 is a flowchart illustrating an RLS determination process according to the second example.

As illustrated in FIG. 14, at S300, a pulse interval is calculated from a pulse signal. At S310, the continuous data of the pulse interval is subjected to a spline interpolation to generate continuous values. Pulse wave interval values every second are calculated (re-sampled), and the calculated pulse wave interval values are subjected to the frequency analysis using CDM.

At S320, the frequency components RLSF (power value) of 0.03 to 0.09 Hz and the frequency components (power value) of 0.09 to 0.4 Hz are obtained. The rate (% RLSF) of the frequency components RLSF of 0.03 to 0.09 Hz is calculated.

That is, the following is calculated: [(Frequency components of 0.03 to 0.09 Hz)/{(Frequency components of 0.03 to 0.09 Hz)+(Frequency components of 0.09 to 0.4 Hz)}]. Furthermore, with respect to the frequency components of less than 0.03 Hz, the accuracy is lower in frequency analysis in comparison with other frequency components. Further, the frequency components of less than 0.03 Hz is greatly influenced when there are symptoms of apnea SAS at the time of the sleep. Thus, the frequency components of less than 0.03 Hz are eliminated from investigation. In addition, the frequency components of greater than 0.4 Hz are also eliminated since those frequency components are scarcely contained in the activity frequency components of autonomic nerve.

At S330, the determination of RLS is made using the value of % RLSF, then ending the present process. In detail, RLS can be determined as follows, using % RLSF during sleep:

No RLS<=0.3;
0.3<RLS complaint with feeling of creepy<0.4;
0.4<RLS with PLMS (without arousal)–Middle<0.5; and
0.5=<RLS with PLMS (with arousal reaction)–Severe RLS.

According to the present example, the determination of RLS can be made in accuracy higher than that in the first example.

Furthermore, for instance, instead of using % RLSF, only a ratio like RLSF/(RLSF+Frequency components of 0.09-0.4 Hz) may be alternatively used. In such a case, the determination can be made as follows:

No RLS<=0.6;
0.6<RLS complaint with feeling of creepy<1;
1<RLS with PLMS (without arousal)–Middle<2; and
2=<RLS with PLMS (with arousal reaction)–Severe RLS.

Third Example

The following explains a third example of the embodiment while omitting portions similar to those of the second example. The present third example includes executions of an clock time-based amendment, and an age-based amendment in addition to the execution or configuration of the second example. Those executions are mainly done by the control circuit 7 functioning as the data analysis device; thus, the control circuit 7 may function as an amendment section to execute a clock time-based or age-based amendment below.

a) Clock Time-Based Amendment

The symptoms of RLS tend to increase (become severe) from the evening and decrease (become mild) towards the dawn. Therefore, the amendment uses the fact that % RLSF changes asymptotically from the time immediately after the sleep onset to the dawn (use of (i) clock time and (ii) time-based variation).

In detail, % RLSF is calculated from the measurement start.

While % RLSF decreases below a half from the time immediately after the sleep onset to the dawn, the doubt of RLS is determined. In such cases, the time immediately after the sleep onset is determined by the decrease of the body movement. The drawn is determined by the recovery of the body movement or clock time.

b) Age-Based Amendment

The power value of the frequency components of RLSF is high when young and decreases with age. Therefore, the degree of RLS can be roughly determined by comparing the absolute value of the power with the age.

For example, the presence of RLS is suspected (i.e., the doubt of RLS is determined) when the average value of one night of the frequency components of RLSF is as follows:

30 or more at the age of 20,
25 or more at the age of 30,
20 or more at the age of 40, and
10 or more at the age of 50.

Furthermore, the tendency of change of the index due to the clock time and age mentioned above is not only limited to the index of RLSF. Since the same tendency can be found even for other indices such as LF and LF/HF, the clock time-based and age-based amendment may be used for other examples including the first example. The indices such as LF and LF/HF is also high when young and decreases with age. The presence of RLS may be suspected when the target index is equal to or greater than a determination value classified using the age and obtained based on an experiment etc., as mentioned above.

Fourth Example

Figure 15:
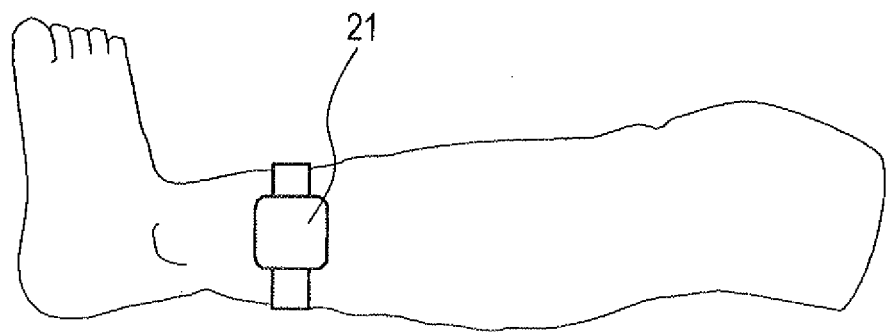
FIG. 15 is a graph illustrating an attachment state of a pulse wave sensor which simultaneously serves as a body motion sensor.

The following explains a fourth example of the embodiment while omitting portions similar to those of the first example. The first to third examples use the pulse wave sensor. In contrast, the present example uses another sensor.

a) Body Motion Sensor (1) With reference to FIG. 15, a pulse wave sensor 21 is attached to a portion of a leg. Such a pulse sensor is designed to also have a function of an acceleration sensor to measure acceleration as a body motion sensor. Thus, the pulse wave and acceleration (i.e., body motion of the portion of the leg) can be measured.

When the body motion sensor detects a periodic motion of the leg, there is a high possibility that the periodic motion corresponds to PLMS caused by RLS. Therefore, (i) the determination of RLS obtained from the pulse wave and (ii) the determination of PLMS obtained from the motion of the leg are synthesized. When both the determinations indicate a possibility of the presence of RLS, the determination of RLS can be considered as having a high reliability.

(2) When the body motion sensor detects again a body motion other than the periodic motion of the portion of the leg, there is a high possibility that the noise due to the body motion overlaps over the pulse wave for the corresponding duration. It is desirable to execute the determination of RLS by excluding the data measured in the corresponding duration.

(3) Furthermore, the variation period of the frequency components of RLSF is compared with the cyclic signal acquired by the body motion sensor, thereby investigating a correlation therebetween. When a possibility that the variation period of the frequency components of RLSF is based on body motion is high, the determination of RLS is made in consideration of that possibility.

For instance, a center frequency is obtained by applying the frequency analysis to a signal obtained from the pulse wave sensor. The center frequency is compared with the frequency components of the acceleration signal obtained from the sensor attached to the leg to thereby determine the accordance of the frequencies thereof. Alternatively, the correlation in respect of the waveform is investigated between the signal from the pulse wave sensor and the acceleration signal, thereby determining the accordance in respect of the clock time when the change or body motion arises.

b) Respiration Sensor

The variation state of the heartbeat interval changes depending on the respiration. In the present example, the determination of RLS is made in consideration of signals from a respiration sensor.

That is, the symptom of the respiration becoming slowly or the symptom of sleep apnea arising may overlap on the frequency range of the low frequency components effective in detecting RLS, thereby affecting the RLS detection. Therefore, in the present example, the frequency components (e.g., 0.02 to 0.03 Hz) due to the respiration and detected by the respiration sensor is omitted; then, the RLS determination is executed.

Fifth Example

The following explains a fifth example of the embodiment while omitting portions similar to those of the first example. The present fifth example detects RLS from the absolute value of the variation amount of the pulse interval without conducting the frequency analysis of the pulse wave interval.

As illustrated in FIGS. 4A, 4B, the RLS patient exhibits a great amount of variation in the pulse interval compared with the normal subject or healthy person. Therefore, when the average or variance of the absolute value of the variation amount of the pulse interval is greater than a reference value, it can be determined that the presence of RLS is suspected, for example.

Other Examples

The present invention need not be limited to the above mentioned examples at all. It can be achieved in various manners within a scope not departing from the present invention.

(1) For example, in the first example, a pulse interval corresponding to a heartbeat interval is obtained by using a pulse wave signal detected by the pulse wave sensor. The presence of RLS is detected from the variation state of the pulse interval.

The electrocardiography sensor can be alternatively used to obtain the heartbeat interval, of which the variation state can be used for the detection of RLS. In addition, the variation state of the continuous blood pressure sensor may be used for the value corresponding to the heartbeat interval.

(2) In addition, the presence of RLS can be detected with much more sufficient accuracy by combining the elements included in the configurations of the above mentioned examples (for example, the amendment method etc.).

(3) Furthermore, the above examples explain the RLS inspection apparatus. Without need to be limited to the above examples, the present invention is also applicable to a program or program product for executing a process based on the above mentioned algorithm or a storage medium which stores such a program or program product.

The storage medium includes various kinds of storage media such as an electronic control unit including a microcomputer, a microchip, a flexible disk, a hard disk, and an optical disk. That is, without need to be limited to the above, any one can be used as the storage medium as long as the program or program product, which executes the process of the RLS inspection apparatus mentioned above, is stored.

[Functions of Control Circuit]

The control circuit 7 functioning as the data analysis device executes the various processes as explained above while including several sections such as an interval calculation section, a variation state calculation section, a comparison section, a determination section, and an amendment section.

The interval calculation section may be configured by S200 or S300 executed by the control circuit 7. The variation state calculation section may be configured by S210 and S220, or S310 and S320 executed by the control circuit 7. The comparison section and determination section may be configured by S260 or S330 executed by the control circuit 7. The amendment section may be configured by the S230, S330 executed by the control circuit 7; further, as explained in the third example, the control circuit 7 may function as an amendment section to execute a clock time-based or age-based amendment.

Each or any combination of processes, functions, sections, steps, or means explained in the above can be achieved as a software section or unit (e.g., subroutine) and/or a hardware section or unit (e.g., circuit or integrated circuit), including or not including a function of a related device; furthermore, the hardware section or unit can be constructed inside of a microcomputer.

Furthermore, the software section or unit or any combinations of multiple software sections or units can be included in a software program, which can be contained in a computer-readable storage media or can be downloaded and installed in a computer via a communications network.

Aspects of the disclosure described herein are set out in the following clauses.

As an aspect of the disclosure, a living body inspection apparatus is provided as follows. An interval calculation section is configured to obtain a heartbeat interval from a signal which indicates a heartbeat variation. A variation state calculation section is configured to calculate an index which indicates a variation state of the heartbeat interval (i.e., heart rate variability (HRV) or heartbeat fluctuation) calculated by the interval calculation section. A comparison section is configured to compare the index, which indicates the variation state of the heartbeat interval calculated by the variation state calculation section, with a predetermined reference value. A determination section is configured to determine a state of a restless legs syndrome, which is represented by RLS, based on a result of comparing by the comparison section.

As an optional aspect, the variation state calculation section may be further configured to: (i) obtain low frequency components, which are within a predetermined frequency range and indicate a sympathetic nerve activity, by conducting a frequency analysis of the heartbeat interval, the low frequency components being represented by LF; and (ii) define, as the index which indicates the variation state of the heartbeat interval, either the low frequency components or a value obtained based on the low frequency components.

The present inventors' research has determined the following: within the frequency components obtained by conducting a frequency analysis of the heartbeat intervals, low frequency components of a predetermined frequency range have a high correlation with the state of RLS.

Therefore, the state of RLS can be detected with sufficient accuracy by using the low frequency components or the related index, which is obtained based on the low frequency components. Furthermore, the low frequency components may be in a range of 0.04 to 0.15 Hz; in detail, a magnitude of a power, or an integral value in the range is used, for instance.

In addition, the relevant index may be an average value of the low frequency components, for example. Further, the variance of the low frequency components becomes greater in the variation than the average, thereby being more advantageous in the detection of the RLS. Furthermore, the frequency analysis for analyzing the variation of the heartbeat intervals includes a well-known FFT (Fast Fourier Transform), and CDM (Complex Demodulation). The CDM needs a shorter processing time, thus being more suitable.

As an optional aspect, the variation state calculation section may be further configured to: (i) obtain low frequency components within a predetermined frequency range and whole frequency components in a whole frequency range, the low frequency components being represented by LF, the whole frequency components being represented by ALL; and (ii) calculate, as the index which indicates the variation state of the heartbeat interval, a ratio of the low frequency components and the whole frequency components, the ratio being represented by LF/ALL.

Under such a configuration, the state of the low frequency components having the high correlation with RLS can be extracted, thus allowing the influence of other disturbances (for example, age) to be eliminated. Furthermore, the very low frequency (VLF) components less than 0.03 Hz (fluctuation components) are found in the test subject diseased of apnea during sleep (sleep apnea syndrome: SAS). When using the whole-frequency components, it is desirable that the very low frequency components be removed with a filter etc.

As an optional aspect, the variation state calculation section may be further configured to: (i) obtain low frequency components within a predetermined frequency range and high frequency components within a predetermined frequency range, the low frequency components being represented by LF, the high frequency components being represented by HF; and (ii) calculate, as the index which indicates the variation state of the heartbeat interval, a ratio of the low frequency components and the high frequency components, the ratio being represented by LF/HF.

Under such a configuration, the state of the low frequency components having the high correlation with RLS can be extracted, thus allowing the influence of other disturbances (for example, age) to be reduced. It is noted that the high frequency components may range from 0.15 to 0.4 Hz, for example.

As a further optional aspect, the frequency range of the low frequency components may be between 0.03 and 0.09 Hz.

The present inventors' research has determined that the symptom of RLS has a high correlation with the low frequency range from 0.03 to 0.09 Hz. Such low frequency components can be used for more accurately detecting RLS.

As a further optional aspect, the variation state calculation section may be further configured to calculate as the index, (i) a ratio of the low frequency components and the high frequency components, the low frequency components being represented by LF, the high frequency components being represented by HF, the ratio being represented by LF/HF, or (ii) a ratio of specific low frequency components of 0.03 to 0.09 Hz and high frequency components, the low frequency components of 0.03 to 0.09 Hz being represented by RLSF, the high frequency components being represented by HF, the ratio being represented by RLSF/HF. The determination section may be further configured to determine the state of the RLS of a test subject based on a result of the comparing by the comparison section using the ratio either LF/HF or RLSF/HF as follows: (i) a normal subject<0.5; (ii) 0.5<RLS complaint alone without periodic limb movements during sleep, which is represented by PLMS<1.0; (iii) 1.0<RLS complaint with PLMS but without arousal<2.0; and (iv) 2.0<RLS complaint with PLMS and arousal or sleep disorder.

Thus, the technique of determining the state of RLS is exemplified using LF/HF or RLSF/HF.

As an optional aspect, the variation state calculation section may be further configured to calculate, as the index which indicates variation state of the heartbeat interval, an absolute value of a variation amount of the heartbeat interval.

The presence or absence, or the degree (severe or mild) of RLS has a high correlation with an absolute value of the variation amount of the heartbeat interval. The presence or absence, or the degree of RLS can be thus easily and sufficiently accurately detected by comparing the absolute value (e.g., an average value, standard deviation) of the variation amount of the heartbeat interval with the reference value.

As an optional aspect, an amendment section may be configured to amend the index, which indicates the variation state of the heartbeat interval calculated by the variation state calculation section, based on an age of a test subject.

Generally, when the young generation or people and elderly generation or people are compared, it is known that the young generation exhibits, for example, the greater variation amount (amplitude) of the heartbeat interval than the elderly generation. Therefore, RLS may be undetectable with sufficient accuracy when only the variation amount of the heartbeat interval is compared with the reference value.

Therefore, the index (for example, the low frequency components) for indicating the variation of the heartbeat interval is amended depending on the age, i.e., the age of the subject. Such a configuration can eliminate an influence of the heartbeat interval resulting from the age, thereby providing a more accurate RLS detection.

It is noted that a method for such an amendment includes, for instance, normalization (for example, LF1/LF2) of the test subjects data (for example, low frequency components LF1) with the data (for example, low frequency components LF2) of the normal subjects of the same age or similar age.

As an optional aspect, an amendment section may be configured to amend the index, which indicates the variation state of the heartbeat interval calculated by the variation state calculation section, based on a clock time when the heartbeat interval is measured.

The symptom of RLS varies during sleep so as to increase from the evening and decrease toward the dawn. Therefore, RLS may be undetectable with sufficient accuracy when only the variation amount of the heartbeat interval is compared with the reference value without consideration of the measurement clock time.

Therefore, the index (for example, the low frequency components) for indicating the variation of the heartbeat interval is amended depending on the measurement clock time, for instance, whether to be evening or dawn. Such a configuration can eliminate an influence of the heartbeat interval resulting from the measurement clock time, thereby providing a more accurate RLS detection.

For instance, the amendment is made as follows. The comparison such as a ratio of measurement data (i.e., the low frequency components or another relevant index) is made, with respect to the same test subject, between the data measured in the evening and the data at dawn. When the data of evening is greater than a predetermined value, the method of determining RLS can be adopted.

As an optional aspect, the determination section may be further configured to determine the state of RLS by considering information based on a signal from a respiration sensor.

The variation state of the heartbeat interval is changed by the respiration. Therefore, it is desirable to determine RLS in consideration of a signal from the respiration sensor.

Usually, the respiration has a frequency of about 0.25 Hz, thus having no influence on the detection of RLS. In cases where the respiration becomes slowly or symptoms of sleep apnea arise, the respiration is overlapped on the low frequency components effective in detecting RLS, thus potentially affecting the detection of RLS.

Thus, for instance, the following is desirable: excluding the frequency components resulting from the respiration using a frequency-dependent filter; then, RLS is determined.

As an optional aspect, the determination section may be further configured to determine the state of RLS by considering information based on a signal from a body motion sensor.

When a body motion arises, the variation state of the heartbeat interval changes. Therefore, it is desirable to determine RLS in consideration of a signal from the body motion sensor. For example, the data obtained during a period for which the body motion is detected is removed for the RLS detection, thereby improving the accuracy of RLS detection.

In addition, a body motion sensor may be an acceleration sensor attached to a leg and able to detect PLMS. In such cases, the use of the outputs of the sensor can more certainly detect RLS.

As an optional aspect, a sensor may be configured to detect a signal which indicates the heartbeat variation.

That is, such a configuration can provide a system equipped with a sensor and an apparatus that processes a signal from the sensor.

It will be obvious to those skilled in the art that various changes may be made in the above-described embodiments of the present invention. However, the scope of the present invention should be determined by the following claims.

What is claimed is:

1. A living body inspection apparatus comprising:
a microcomputer configured to
obtain a heartbeat interval from a signal which indicates a heartbeat variation;
obtain low frequency components (LF), which are within a predetermined frequency range, by conducting a frequency analysis of the heartbeat interval;
obtain high frequency components (HF), which are within a predetermined frequency range, by conducting a frequency analysis of the heartbeat interval;
define as an index a ratio of the low frequency and the high frequency components, the ratio being represented by LF/HF, wherein the index indicates a variation state of the heartbeat interval;

compare the index, which indicates the variation state of the heartbeat interval, with a predetermined reference value; and determine an occurrence of restless leg syndrome, which is represented by RLS, and if said occurrence of RLS is accompanied by an occurrence of a periodic limb movement, an arousal event, a sleep disorder or a combination of at least two of the periodic limb movement, the arousal event or the sleep disorder based on a result of comparing the index with a predetermined reference value.

2. The living body inspection apparatus according to claim 1, wherein the frequency range of the low frequency components is between 0.03 and 0.09 Hz.

3. The living body inspection apparatus according to claim 1,

The microcomputer being further configured to calculate as the index either, the ratio
LF/HF, or a ratio of specific low frequency components of 0.03 to 0.09 Hz and high frequency components, the low frequency components of 0.03 to 0.09 Hz being represented by RLSF, the high frequency components being represented by HF, the ratio being represented by RLSF/HF, the determining an occurrence of RLS further including using the ratio either LF/HF or RLSF/HF to determine if said occurrence of RLS is accompanied by an occurrence of a periodic limb movement, an arousal event, a sleep disorder or a combination of at least two of the periodic limb movement, the arousal event or the sleep disorder as follows:

a normal subject<0.5;

0.5<=and <1.0, RLS complaint alone without periodic limb movements during sleep, which is represented by PLMS;

1.0<=and <2.0, RLS complaint with PLMS but without arousal;

2.0<=, RLS complaint with PLMS and arousal or sleep disorder.

4. The living body inspection apparatus according to claim 1, wherein the microcomputer is further configured to amend the index, which indicates the variation state of the heartbeat interval, based on an age of a test subject.

5. The living body inspection apparatus according to claim 1, wherein the microcomputer is further configured to amend the index, which indicates the variation state of the heartbeat interval, based on a clock time when the heartbeat interval is measured.

6. The living body inspection apparatus according to claim 1, the microcomputer being further configured to determine the occurrence of RLS by considering information based on a signal from a respiration sensor communicably coupled to the living body inspection apparatus.

7. The living body inspection apparatus according to claim 1, the microcomputer being further configured to determine the occurrence of RLS by considering information based on a signal from a body motion sensor communicably coupled to the living body inspection apparatus.

8. The living body inspection apparatus according to claim 1, further comprising:

a sensor configured to detect a signal which indicates the heartbeat variation.

9. A method for determining a degree of a restless leg syndrome, which is represented by RLS, using a living body inspection apparatus including a microcomputer, the method comprising:

using the microcomputer to obtain a heartbeat interval from a signal which indicates a heartbeat variation;

using the microcomputer to obtain low frequency components (LF), which are within a predetermined frequency range, by conducting a frequency analysis of the heartbeat interval;

using the microcomputer to obtain high frequency components (HF), which are within a predetermined frequency range, by conducting a frequency analysis of the heartbeat interval;

using the microcomputer to compare the index, which indicates the variation state of the heartbeat interval, with a predetermined reference value; and using the microcomputer to determine an occurrence of restless leg syndrome, which is represented by RLS, and if said occurrence of RLS is accompanied by an occurrence of a periodic limb movement, an arousal event, a sleep disorder or a combination of at least two of the periodic limb movement, the arousal event or the sleep disorder based on a result of comparing the index with a predetermined reference value.

10. A program product stored in a non-transitory computer readable storage medium comprising instructions for execution by a computer, the instructions including the method according to claim 9, which is computer-implemented.

* * * * *